US010357211B2

(12) United States Patent
Smith et al.

(10) Patent No.: US 10,357,211 B2
(45) Date of Patent: *Jul. 23, 2019

(54) METHOD FOR DUAL ENERGY AND/OR CONTRAST ENHANCED BREAST IMAGING FOR SCREENING, DIAGNOSIS AND BIOPSY (71) Applicant: Hologic, Inc., Bedford, MA (US)

(72) Inventors: Andrew P. Smith, Lexington, MA (US); Jay A. Stein, Boston, MA (US); Zhenxue Jing, Chadds Ford, PA (US); Baorui Ren, Andover, MA (US); Loren Niklason, N Tetonia, ID (US); Christopher Ruth, Boxford, MA (US); Ian Shaw, Yorktown Heights, NY (US)

(73) Assignee: HOLOGIC, INC., Marlborough, MA (US)

( * ) Notice: Subject to any disclaimer, the term of this patent is extended or adjusted under 35 U.S.C. 154(b) by 1033 days.

This patent is subject to a terminal disclaimer.

(21) Appl. No.: 14/695,090

(22) Filed: Apr. 24, 2015

(65) Prior Publication Data
US 2015/0327826 A1 Nov. 19, 2015

Related U.S. Application Data (63) Continuation of application No. 13/415,675, filed on Mar. 8, 2012, now Pat. No. 9,020,579.
(Continued)

(51) Int. Cl.
A61B 6/00 (2006.01)
A61B 6/02 (2006.01)
(Continued)

(52) U.S. Cl.
CPC ............ *A61B 6/025* (2013.01); *A61B 6/4417* (2013.01); *A61B 6/463* (2013.01); *A61B 6/466* (2013.01);
(Continued)

(58) Field of Classification Search
CPC ........... A61B 10/04; A61B 6/025; A61B 6/12; A61B 6/4035; A61B 6/4417; A61B 6/463; A61B 6/466; A61B 6/481; A61B 6/482; A61B 6/502; A61B 6/5235; A61M 5/007; F04C 2270/041
See application file for complete search history.

(56) References Cited

U.S. PATENT DOCUMENTS 7,245,694 B2 7/2007 Jing
7,702,142 B2 4/2010 Ren
(Continued)

FOREIGN PATENT DOCUMENTS

JP 2006-519634 8/2006
JP 2007-130487 5/2007
(Continued)

OTHER PUBLICATIONS

PCT/US12/28334 International Search Report and Written Opinion, dated Jul. 5, 2012.
(Continued)

Primary Examiner — Amelie R Gillman (57) ABSTRACT

Systems and methods for x-ray imaging a patient's breast in combinations of dual-energy, single-energy, mammography and tomosynthesis modes that facilitate screening for and diagnosis of breast abnormalities, particularly breast abnormalities characterized by abnormal vascularity.

18 Claims, 10 Drawing Sheets

Related U.S. Application Data (60) Provisional application No. 61/450,304, filed on Mar. 8, 2011.

(51) Int. Cl.
  *A61M 5/00* (2006.01)
  *A61B 10/04* (2006.01)
  *A61B 6/12* (2006.01)

(52) U.S. Cl.
  CPC .............. *A61B 6/481* (2013.01); *A61B 6/482* (2013.01); *A61B 6/502* (2013.01); *A61B 6/5235* (2013.01); *A61B 10/04* (2013.01); *A61M 5/007* (2013.01); *A61B 6/12* (2013.01); *A61B 6/4035* (2013.01); *F04C 2270/041* (2013.01)

(56) References Cited

U.S. PATENT DOCUMENTS

| | | | |
|---|---|---|---|
| 7,760,924 | B2 | 7/2010 | Ruth |
| 7,869,563 | B2 | 1/2011 | DeFreitas |
| 7,991,106 | B2 | 8/2011 | Ren |
| 8,594,274 | B2 | 11/2013 | Hoernig |
| 2004/0127789 | A1 | 7/2004 | Ogawa |
| 2005/0113681 | A1 | 5/2005 | DeFreitas |
| 2006/0025680 | A1 | 2/2006 | Jeune |
| 2006/0269040 | A1 | 11/2006 | Mertelmeier |
| 2007/0019846 | A1 | 1/2007 | Bullitt |
| 2007/0114424 | A1 | 5/2007 | Danielsson |
| 2008/0019581 | A1 | 1/2008 | Gkanatsios |
| 2008/0152086 | A1 | 6/2008 | Hall |
| 2009/0003519 | A1 | 1/2009 | DeFreitas |
| 2009/0296882 | A1 | 12/2009 | Gkanatsios |
| 2010/0135558 | A1 | 6/2010 | Ruth |
| 2011/0069808 | A1 | 3/2011 | DeFreitas |
| 2012/0134464 | A1 | 5/2012 | Hoernig |

FOREIGN PATENT DOCUMENTS

| | | |
|---|---|---|
| JP | 2009-522005 | 6/2009 |
| WO | 2010/028208 A1 | 3/2010 |

OTHER PUBLICATIONS

EP Extended Search Report dated Jul. 18, 2014 in EP App 12754521.8.
Weidner N, et al, Tumor angiogenesis and metastasis: correlation in invasive breast carcinoma. NEJM 1991; 324:1-8.
Weidner N, The importance of tumor angiogenesis: the evidence continues to grow. AM J Clin Pathol. Nov. 2004 122(5):696-703.
Lehman CD, et al., MRI evaluation of the contralateral breast in women with recently diagnosed beast cancer.
Lindfors KK, et al., Dedicated breast CT: initial clinical experience. Radiology 2008; 246(3): 725-733.
Prionas ND, et al., Contrast-enhanced dedicated breast CT: initial clinical experience. Radiology. Sep. 2010 256(3):714-723.
Chen SC, et al., Initial clinical experience with contrast-enhanced digital breast tomosynthesis. Acad Radio. Feb. 2007 14(2):229-38.
Carton AK, et al., Dual-energy contrast-enhanced digital breast tomosynthesis—a feasibility study. BR J Radiol. Apr. 2010;83(988):344-50.
Lewin JM, et al., Dual-energy contrast-enhanced digital subtraction mammography: feasibility. Radiology 2003; 229:261-268.
Jong, RA, et al., Contrast-enhanced digital mammography: initial clinical experience. Radiology 2003; 228:842-850.
Diekmann F., et al., Digital mammography using iodine-based contrast media: initial clinical experience with dynamic contrast medium enhancement. Invest Radiol 2005; 40:397-404.
Dromain C., et al., Contrast-enhanced digital mammography. Eur J Radiol. 2009; 69:34-42.
Dromain C., et al. Contrast enhanced spectral mammography: a multi-reader study, RSNA 2010, 96th Scientific Assembly and Scientific Meeting.
Jochelson M., et al, RSNA 2010, 96th Scientific Assembly and Scientific Meeting.
Niklason, L., et al., Digital tomosynthesis in breast imaging. Radiology. Nov. 1997; 205(2):399-406.
Kopans, et al., Will tomosynthesis replace conventional mammography? Plenary Session SFN08:RSNA 2005.
Smith, A., Full field breast tomosynthesis. Radiol Manage. Sep.-Oct. 2005; 27(5):25-31.
Poplack SP, et al, Digital breast tomosynthesis: initial experience in 98 women with abnormal digital screening mammography. AJR Am J Roentgenology Sep. 2007 189(3):616-23.
Freiherr G. Breast tomosynthesis trials show promise. Diagnostic Imaging—San Francisco 2005, V27; N4:42-48.
Rafferty E. et al. Assessing Radiologist Performance Using Combined Full-Field Digital Mammography and Breast Tomosynthesis Versus Full-Field Digital Mammography Alone: Results . . . presented at 2007 Radiological Society of North America meeting, Chicago IL.
Berg WA et al. Combined screening with ultrasound and mammography vs mammography alone in women at elevated risk of breast cancer. JAMA 299:2151-2163, 2008.
ICRP Publication 60: 1990 Recommendations of the International Commission on Radiological Protection.
Giger, M. et al., Development of a smart workstation for use in mammography, Proceedings of SPIE, (1991), 45:101-103.
Giger, M. et al., An Intelligent Workstation for Computer-aided Diagnosis, RadioGraphics, (1993), 13(3): 657-656.

Projection Image Customization Table

| # | Kv | mA | Filter | Start Time | Duration | Compression |
|---|----|----|--------|------------|----------|-------------|
| 1 |    |    |        |            |          |             |
| 2 |    |    |        |            |          |             |
| 3 |    |    |        |            |          |             |
| .. |   |    |        |            |          |             |

METHOD FOR DUAL ENERGY AND/OR CONTRAST ENHANCED BREAST IMAGING FOR SCREENING, DIAGNOSIS AND BIOPSY

REFERENCE TO RELATED APPLICATIONS

This application is a continuation application of U.S. patent application Ser. No. 13/415,675, filed Mar. 8, 2012, now U.S. Pat. No. 9,020,579, issued Apr. 28, 2015, which claims priority under 35 U.S.C. § 119 from provisional U.S. Patent Application Ser. No. 61/450,304 filed Mar. 8, 2011, the contents of which are incorporated herein by reference.

FIELD

This patent specification relates to medical imaging and more specifically to a system that enables selection among a plurality of different imaging modes, a plurality of different imaging processes, image acquisition parameters and image processing techniques.

BACKGROUND

Several references are listed at the end of the disclosure portions of this patent specification and are referred to below by numbers in parenthesis. These references a well as prior patents identified in this patent specification are hereby incorporated by reference.

In the U.S. breast cancer mortality is second only to that of lung cancer for women. Because of its role in early tumor detection, x-ray mammography has become them most commonly used tool for breast cancer screening, diagnosis and evaluation in the United States. A mammogram is an x-ray image of inner breast tissue that is used to visualize normal and abnormal structures within the breasts. Mammograms provide early cancer detection because they can often show breast lumps and/or calcifications before they are manually palpable.

While screening x-ray mammography is recognized as the most effective method for early detection of breast cancer, it also presents challenges in that in some cases it may be difficult to determine whether a detected abnormality is associated with a cancerous or benign lesion. One reason for this is that a mammogram Mp is a two dimensional projection image representating a three dimensional structure, and overlapping structures in the compressed breast may confound image interpretation and diagnosis. A second reason is that the x-rays that are often used to obtain the images have energies that are in a range that helps achieve a desirable Signal to Noise Ratio (SNR) but at the same time may cause the x-rays to be attenuated to a similar degree by breast structures that may have different clinical significance.

Efforts to improve the sensitivity and specificity of breast x-rays have included the development of breast tomosynthesis systems. Breast tomosynthesis is a three-dimensional imaging technology that involves acquiring images of a stationary compressed breast at multiple angles during a short scan. The individual projection tomosynthesis images Tp taken at respective angles of the imaging x-ray beam relative to the breast are then computer-processed into a series of reconstructed tomosinthesis slice images Tr each representing a respective slice of the breast. The Tp and/or Tr images can be displayed individually or concurrently or in a dynamic cine mode. Breast tomosynthesis mammography [see references 14-19] typically uses a field digital mammography (FFDM) platform. In one example, an x-ray tube moves in an arc above the breast and a series of 11 to 22 low dose x-ray 2-D tomosynthesis projection images Tp is obtained. The sum of the dose from all of the 2-D tomosynthesis projection images Tp is similar to the dose from a single conventional digital mammogram Mp. These low-dose 2-D tomosynthesis projection images Tp are reconstructed into a series of 3-D slice images Tr each representing a slice of the breast where each slice is, for example, 1-5 mm thick. The slice images typically conform to planes parallel to the platform supporting the breast during image acquisition, but could be oriented differently. An advantage of breast tomosynthesis compared to conventional mammography is that by showing the breast as a series of slices rather than a single mammogram, a lesion may be seen with greater clarity because much of the superimposed tissue present in a conventional mammogram has been removed.

Reconstructed tomosynthesis slice images Tr reduce or eliminate problems caused by tissue overlap and structure noise in two-dimensional mammography imaging. Digital breast tomosynthesis also offers the possibility of reduced breast compression, improved diagnostic and screening accuracy, fewer recalls, and 3D lesion localization. An example of a multi-mode breast tomosynthesis/mammography system is described in commonly assigned U.S. Pat. No. 7,869,563. Other aspects of breast tomosynthesis and mammography are described in commonly assigned U.S. Pat. Nos. 7,991,106, 7,760,924, 7,702,142, and 7,245,694, which are hereby incorporated by reference.

In an effort to address challenges in differentiating breast cancer from benign abnormalities in breast x-ray imaging, consideration has been given to contrast-enhanced and dual-energy imaging. In contrast-enhanced imaging, a contrast agent that may be iodine-based is introduced into the breast, typically through an injection in a vein remote from the breast, and x-ray images are taken after (as well as possibly before) the contrast agent has reached the breast. The contrast agent helps highlight vascularity in the breast. If images of the same breast taken before and after the arrival of the contrast agent in the breast are subtracted from each other (and absent breast motion between the times the two images are taken), breast vascularity may be appear even more clearly in the resulting subtraction image. This may assist in differentiating cancer from benign tissue because it is believed that breast cancers release angiogenesis factors that increase the formation of small vessels near the tumor (1, 2). (The Arabic numbers in parenthesis refer to respective publications listed at the end of this patent specification.) It is believed that the growth of breast cancer is dependent on angiogenesis, and that these vessels differ from normal vessels in that they have increased permeability and are often tortuous. Imaging of the vessels around a tumor is believed to allow improved detection of breast cancer.

MRI (Magnetic Resonance Imaging) can be used with contrast enhancement to help characterize breast cancers by imaging the vascular network near a breast cancer (3). Although contrast enhanced breast MRI (CEMRI) can be effective in imaging breast cancer it has limitations including high cost, long procedure time, enhancement of benign abnormalities such as fibroadenomas, and inability to image women with metal clips or claustrophobia. Typically, the contrast agent used in CEMRI is gadolinium-based and is different from the contrast agents used in x-ray imaging.

X-ray imaging also can use contrast enhancement to improve cancer detection. The use of contrast agents such as iodine with x-ray methods has been suggested for imaging the vascular network near a breast cancer. These x-ray imaging methods include breast CT (4, 5), breast tomosynthesis (6, 7) and digital mammography (8-13). Contrast enhanced x-ray mammography (CEM) may improve the conspicuity of breast cancers (8-13). It has also been suggested that CEM may provide improved specificity compared to CEMRI because fewer benign lesions enhance (13). These studies are small and may need to be validated with larger trials.

In x-ray mammography, contrast enhanced mammography has been evaluated using two methods. The first involves subtraction of images obtained pre- and post-contrast (9). This method is referred to as time subtraction. The second method is referred to as dual-energy contrast imaging. In this method images are obtained at low energy and high energy after the injection of contrast. The images are obtained at energies above and below the k-edge of iodine (33.2 keV) when iodine-based contrast agent is used. At x-ray energies just above the k-edge the absorption of x-rays is increased resulting in an increase of contrast from the iodine contrast agent in the high energy image. Subtraction of these two images enhances iodine contrast while suppressing the contrast of normal breast anatomy. An advantage of dual-energy contrast imaging mammography is that both images may be obtained in a very short time and therefore the images may be subtracted with little patient motion. This is not true for subtraction of pre- and post-contrast images since typically there will be more than a minute separating the acquisition of the two images.

One goal of any x-ray imaging system is to obtain the highest quality images to reduce the occurrence of false positive and false negative diagnoses. It would be desirable to identify a system and method for acquiring x-ray images to alleviate issues associated with specificity and sensitivity in current designs.

SUMMARY OF THE DISCLOSURE

The patent specification describes x-ray imaging systems and methods that facilitate x-ray screening and diagnosis of patients, particularly of patients' breasts, and particularly for abnormalities characterized by suspicious vascularity. In a non-limiting example, combination of imaging modes are used, preferably in a single breast compression, to obtain a collection of x-ray images that provide unexpectedly better facility of screening and diagnosis of such abnormalities. As one example, the new system and method are used to image a patient's breast after an x-ray contrast agent has been introduced in the breast. A selected time after injecting the contrast agent, the system obtains 3D slice images representing respective slices of a patient's breast. These 3D slice images are formed by computer-processing, through a reconstruction algorithm, a multiplicity of x-ray 2D tomosynthesis projection images of the breast taken at respective angles of an imaging x-ray beam to the breast. The system also obtains a 2D combination image of a low-energy 2D x-ray mammogram and a high-energy 2D x-ray mammogram of the breast. These 2D projection images and low-energy and high-energy mammograms preferably are obtained in a single compression of the patient's breast. The system displays, preferably concurrently, the 2D combination image and one or more of the 3D slice images. The displayed combination 2D image facilitates identification of a position of a possible vascular abnormality in two dimensions, and the 3D slice images facilitate identification of the position of the abnormality in three dimensions and enables visualization of the appearance of the abnormality in respective slice images.

These and other aspects of the system and method are further explained in the detailed description that follows and in the appended drawings.

DETAILED DESCRIPTION OF ILLUSTRATIVE EMBODIMENTS

The examples of systems and methods described in this patent specification leverage and combine advantages of one or more image acquisition modes, including two-dimensional (2D), three-dimensional (3D), dual-energy (DE) and contrast-enhancement (CE) imaging to provide a breast imaging system with improved sensitivity and specificity and with benefits for more efficacious screening and diagnosis, greater convenience for the radiologist and better patient workflow.

A system according to one example includes an x-ray source including one or more x-ray filters, an imaging x-ray detector, and an immobilization mechanism positioned between the x-ray source and the detector for immobilizing an object to be imaged such as a patient's breast. During image acquisition, X-rays of two or more different energy ranges are generated from the x-ray source by varying at least one x-ray source acquisition parameter, including but not limited to the x-ray filters and x-ray kV. The x-rays propagate through the imaged object and are received by the detector. The composition of the imaged object modulates the x-rays through mechanisms such as attenuation, absorption and scatter, resulting in relatively brighter and darker areas in a detected image. The detected image is processed using computer-processing techniques and the resulting images may be stored and/or displayed at a radiologist's workstation.

The system may include a control module for controlling image acquisition, the control module including a user interface permitting a user to select one or more modes of image acquisition and/or image processing. The user interface may comprise a key pad, touch pad, joystick or other input mechanism that interacts with a computer program executing on a computer system coupled to a display. Such a user interface may enable selection of image acquisition mode, such as a 2D mammography mode, a 3D tomosynthesis imaging mode or a combination 2D/3D imaging mode depending upon the capabilities of the breast imaging device.

Alternatively (or in combination) the interface may enable further customization of image acquisition via selection of particular acquisition parameters and acquisition processes within each selected imaging mode. For example, the system is adapted to implement a dual-energy image acquisition process for at least one image acquired in 2D, 3D or a combination (combo) mode. In addition, the system ay be configured to perform a background subtraction image acquisition process for images acquired in dual-energy 2D, 3D and/or combo modes.

In addition to enabling the selection of various imaging processes within each image mode, the system may be configured to enable a user to customize the acquisition parameters of a given mode or process. Thus the system may further allow the user to identify acquisition parameters such as contrast agent, kV, mA, image timing, and x-ray filter type. As will be described in more detail later herein, the selection of parameters may be varied between different 2D image acquisitions, such as between sequential projection images Tp during a tomosynthesis acquisition, and to trigger imaging in relation to the timing of introducing a contrast agent.

In addition to enabling selection of acquisition modes and operating parameters, the user interface may allow selection of various forms of image processing that are to be used on the captured image, including a 3D reconstruction process (backward projection, forward projection, with weighting, etc.), noise filtering algorithms, subtraction of different energy images with or without differential weighting, addition of different energy images with or without differential weighting, etc. Alternatively, the control module may be programmed to select a preferred method of image processing in accordance with a selected acquisition mode, or in accordance with a selected operating parameter, or a combination thereof.

These and other features will now be described in greater detail with regard to the figures.

Image Acquisition

One example is an x-ray image acquisition system that is optimized for mammography and breast tomosynthesis and is further modified for dual-energy imaging and for the use of a contrast agent. One system that can serve as a basis for further modifications is the Selenia® Dimensions® tomosynthesis imaging system, manufactured and sold by Hologic, Inc., of Bedford Mass. This system is a combo-mode system capable of acquiring images in either or both 2D and 3D mode, but it should be clear that this is not the only example of a suitable system, that tomosynthesis-only systems also may serve as a basis for modification, and that some aspects of mammography-only systems also may be useful as a basis for further modifications. Accordingly, the systems and methods described in this patent specification are not limited to a particular starting system that can be used or modified to carry out the required processes. Certain aspects of examples of a starting system are described in the commonly owned patents cited above.

Figure 1:
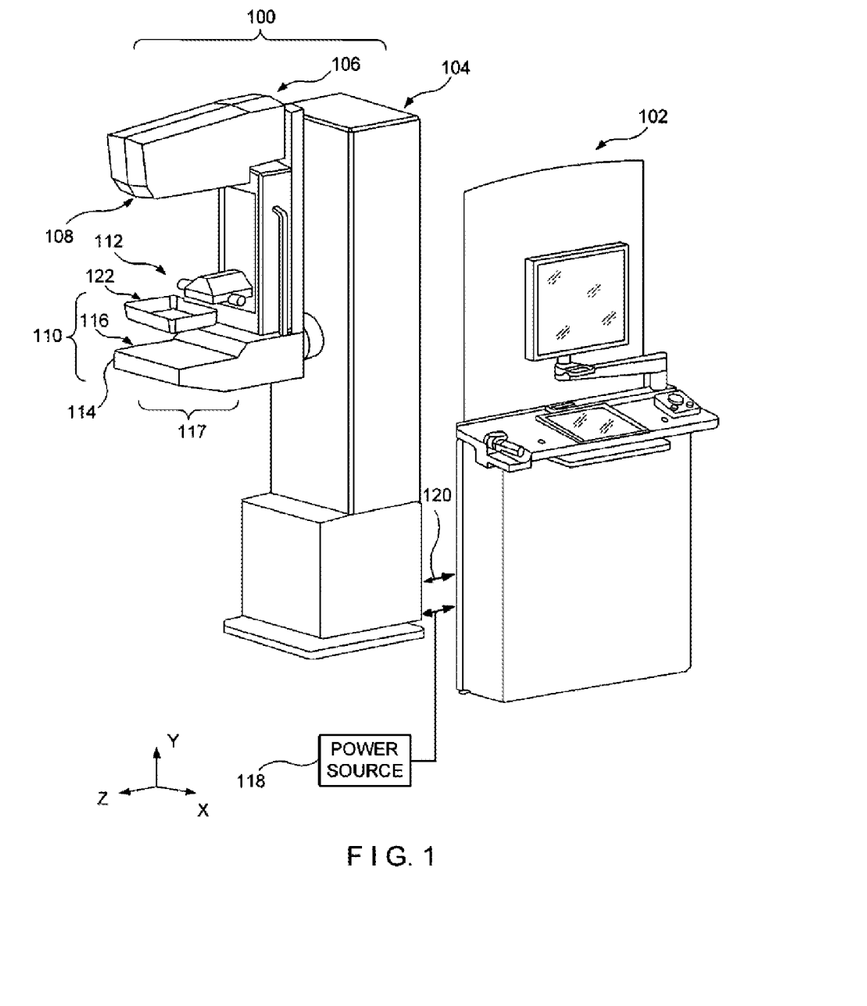
FIG. 1 illustrates an x-ray breast imaging system that provides a choice of multiple imaging modes including a 3D tomosynthesis mode and a 2D mammography mode, in each case using single-energy imaging of dual-energy imaging, and in each case with or without a contrast agent in the breast.
Figure 2:
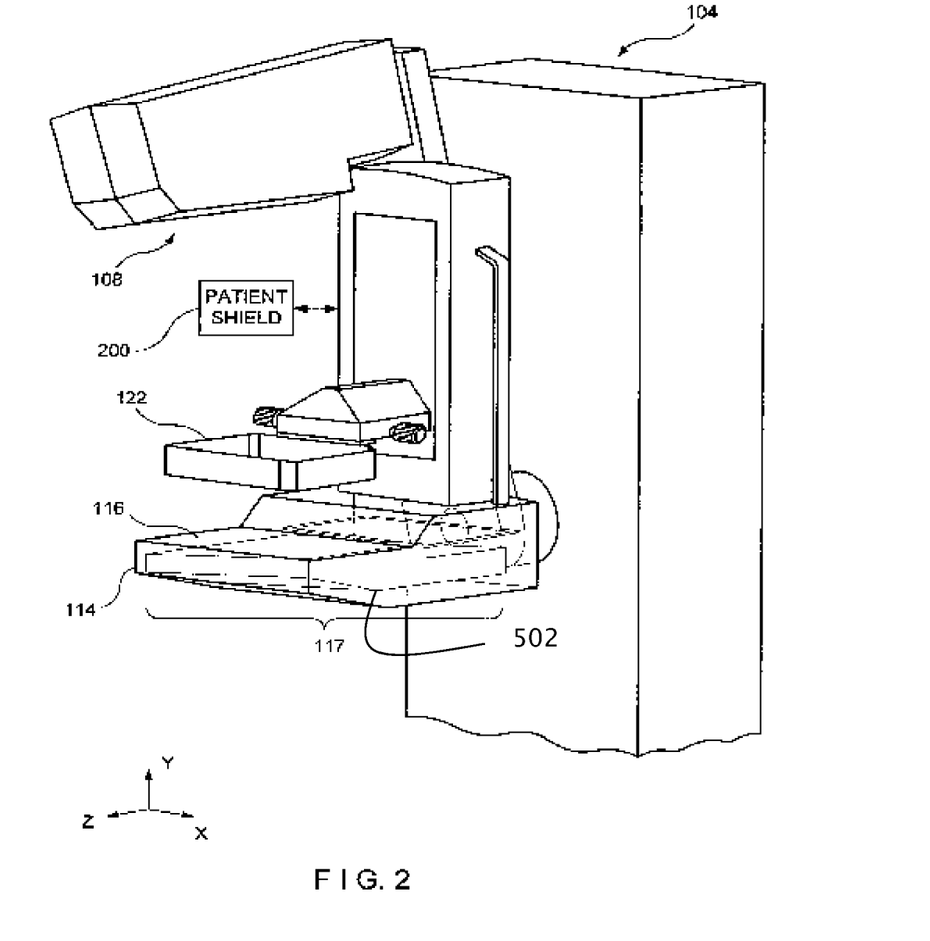
FIG. 2 illustrates in greater detail a portion of the FIG. 1 system.
Figure 3:
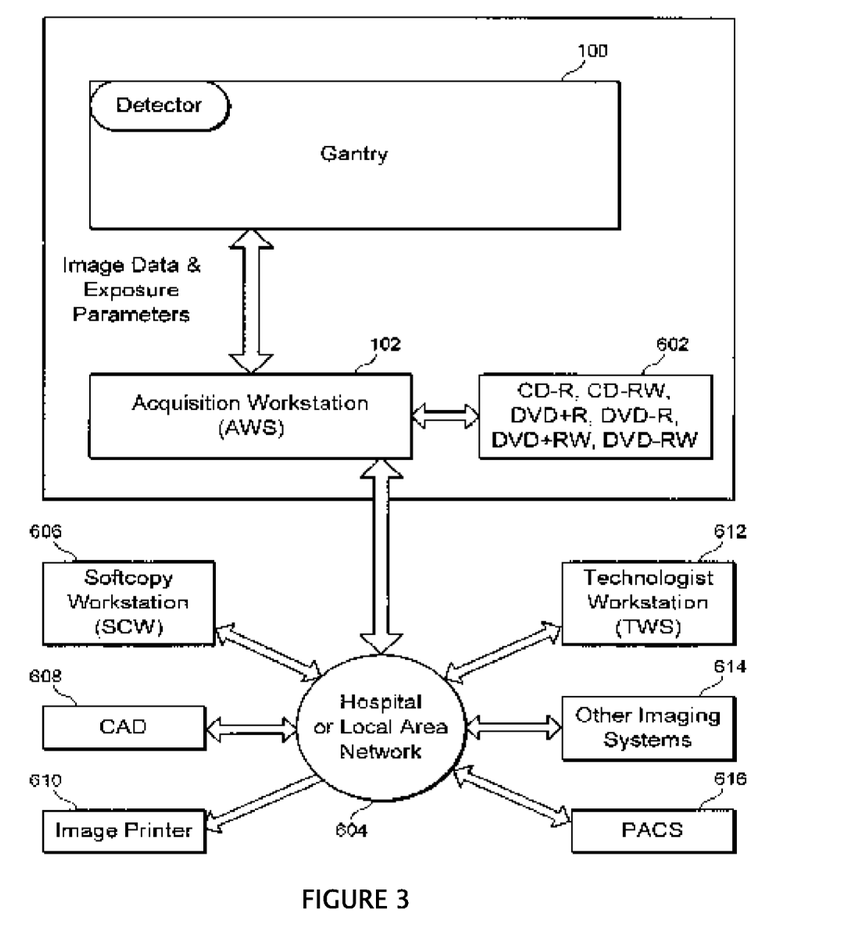
FIG. 3 illustrates further aspects of the FIG. 1 system.

FIGS. 1-3 illustrate various components of a non-limiting example of a multi-mode mammography/tomosynthesis system that can carry out the processes described in this patent specification with suitable additions or modification for dual-energy imaging described below. The system comprises a gantry 100 and a data acquisition work-station 102. Gantry 100 includes a housing 104 supporting a tube arm assembly 106 rotatably mounted thereon to pivot about a horizontal axis 402 and carrying an x-ray tube assembly 108. X-ray tube assembly 108 includes (1) an x-ray tube generating x-ray energy in a selected range, such as 20-50 kV, at mAs such as in the range 3-400 mAs, with focal spots such as a nominal size 0.3 mm large spot and nominal size 0.1 mm small spot (2) supports for multiple x-ray filters such as molybdenum, rhodium, aluminum, copper, cesium iodide, silver and tin filters, and (3) an adjustable collimation assembly selectively collimating the x-ray beam from the focal spot in a range such as from a 7 by 8 cm rectangle to a 24 by 29 cm rectangle when measured at the image plane of an x-ray image receptor 502 included in the system, at a maximum source-image distance such as 75 cm. Also mounted on housing 104, for rotation about the same axis 402 (or a different axis), is a compression arm assembly 110 that comprises a compression plate or paddle 122 and a receptor housing 114 having an upper surface 116 serving as a breast plate or platform and enclosing an image detector subsystem system 117 comprising a flat panel x-ray imaging receptor 502 (FIG. 2), a retractable anti-scatter grid, and a mechanism for driving and retracting anti-scatter grid between a position in which the imaging x-ray beam passes through the grid and a position in which the grid is outside the imaging x-ray beam. Housing 104 also encloses a vertical travel assembly 404 for moving tube arm assembly 106 and compression arm assembly 110 up and down to accommodate a particular patient or imaging position, a tube arm assembly rotation mechanism to rotate tube arm assembly 106 about the horizontal axis for different imaging positions, a detector subsystem rotation mechanism for rotating components of detector subsystem 117 about the horizontal axis to accommodate different operations modes, and a couple/uncouple mechanism to selectively couple or uncouple tube arm assembly 106 and compression arm assembly 110 to and from each other, and tube arm assembly 106 and detector subsystem 117 to and from each other. Housing 104 also encloses suitable motors and electrical and mechanical components and connections to implement the functions discussed here. A patient shield 200, schematically illustrated in FIG. 2, can be secured to compression arm assembly 110 to provide a mechanical interlock against patient contact with the rotating x-ray tube arm assembly 106. Work-station 102 comprises components similar to those in the Selenia® mammography system and in the Selenia® Dimensions® combo system, including a display screen (typically a flat panel display that may include touch-screen functionality), user interface devices such as a keyboard, possibly a touch-screen, and a mouse or trackball, and various switches and indicator lights and/or displays. Work-station 102 also includes computer facilities similar to those of the Selenia® and the Selenia® Dimensions® system (but adapted through hardware, firmware and software differences) for controlling gantry 100 and for processing, storing and displaying data received from gantry 100. A power generation facility for x-ray tube assembly 108 may be included in housing 104 or in work-station 102. A power source 118 powers work-station 102. Gantry 100 and work-station 102 exchange data and controls over a schematically illustrated connection 120.

As illustrated in FIG. 3, additional storage facilities 602 can be connected to work-station 102, such as one or more optical disc drives for storing information such as images and/or for providing information to work-station 102 such as previously obtained images and software, or a local printer (not shown). In addition, the disclosed system can be connected to a hospital or local area or other network 604, and through the network to other systems such as a soft copy workstation 606, a CAD (Computer Aided Detection) station 608 for computer-processing mammography and/or tomosynthesis images to identify likely abnormalities, an image printer 610 for printing images, a technologist workstation 612, other imaging systems 614 such as other mammography systems or systems for other modalities for exchange of images and/or other information, and to a PACS (Picture Archiving) systems 616 for archiving images and other information and/or retrieving images and other information.

In standard mammography mode, typically used for screening mammography, tube arm assembly 106 and compression arm assembly 110 are coupled and locked together in a relative position such as seen in FIG. 1, such that an x-ray beam from x-ray tube assembly 108 illuminates x-ray receptor 502 when the patient's breast is compressed by compression device 112. In this mode, the system operates in a manner similar to said Selenia® system to take a mammogram. Vertical travel assembly 404 and tube arm rotation mechanism can make vertical adjustments to accommodate a patient, and can rotate tube arm assembly 106 and compression arm assembly 110 together as a unit about the horizontal axis for different image orientations such as for CC and for MLO images. For example, tube arm assembly 106 and compression arm assembly 110 can rotate between (−195.degree.) and (+150.degree.) about the axis. As in the Selenia® system, compression device 112 includes a compression paddle 122 that can move laterally, in a direction along the chest wall of a patient, to adjust for different imaging orientations. The compression paddle may comprise any one of a plurality of types of paddles, including but not limited to a fill paddle, a spot paddle, or a curved paddle (which may be preferred for use in contrast image acquisition processes described below), and may be configured to tilt against a spring bias and/or to move laterally, as described in the commonly owned patents identified above.

In tomosynthesis mode, as used for example in said Selenia® Dimensions® system and as described in said U.S. Pat. No. 7,869,563, tube arm assembly 106 and compression arm assembly 110 are decoupled such that compression arm assembly 110 stays in one position, compressing the patient's breast, while tube arm assembly 106 rotates about the horizontal axis, for example +/−15 degrees relative to compression arm assembly 110. Tomosynthesis can be carried out for different image orientations, so that compression arm assembly 110 can be rotated about the horizontal axis (alone or together with assembly 106) for a desired image orientation and locked in place, and then tube arm assembly 106 can be rotated relative to that position of compression arm assembly 110 for tomosynthesis imaging over +/−15 degree or some other desired angular range. For example, low dose tomosynthesis may be performed over a seven degree angular range to collect in the area of seven projection images.

In a combination mode, during a single compression of the patient's breast the system takes a conventional mammogram and tomosynthesis images. In this mode, while the breast remains compressed in compression arm assembly 110, (1) tube arm assembly 106 sweeps and x-ray receptor 502 rocks, each through an appropriate angle, and x-ray exposures are taken for tomosynthesis images, and (2) a standard mammogram is taken. The standard mammogram can be taken at a 0 (zero) degree angle relative angle between tube arm assembly 106 and a normal to the imaging plane of x-ray receptor 502, and can be taken before or after the tomosynthesis images are taken or between the taking of two successive tomosynthesis images. Typically, each tomosynthesis image utilizes substantially lower x-ray dose than the standard mammogram.

For example, as described above, the total dosage of all projection images taken during the tomosynthesis scan can range from 0.25 to 2.0 times that of the dose of a single mammogram. The relationship between the two dosages can be user-selected to control any one of the x-ray tube voltage, current, tomosynthesis scan angle, number of projection images obtained, etc. In alternate embodiments, the dosage may be altered via a simple switch on the gantry, or through a user control at a radiologist workstation. In still alternate embodiments the dosage may vary automatically as the radiologist switches between modes.

Image Acquisition Process Selection

One important characteristic of any digital imaging system is the ability to vary the amount and intensity of radiation used to generate any image. Radiation intensity is related to the atomic number (Z) of the x-ray target, the x-ray current (mA), x-ray voltage and x-ray beam filtration. Radiation intensity, is varied to improve image quality, which in turn can improve diagnostic sensitivity. When radiation intensity increases, quantum mottle (image noise caused by photon absorption) tends to decrease and vice versa.

Many mammography and tomosynthesis systems allow the operator to control x-ray exposure by manually setting technique factors such as mA and mSec. Some systems include an Automatic Exposure Control (AEC) functionality which controls a duration of administration of radiation, turning off the x-ray source when the desired dose has been administered. Automatic Exposure Control (AEC) methods may vary the dosing parameters, including exposure time, kV, mA and filter modes for an image to vary the exposure and the radiation intensity.

While such control over acquisition parameters may provide some improvement over image quality, according to one aspect of the system and method described in this patent specification, improved image quality may be provided by incorporating additional acquisition processes into 2D, 3D or combo systems to realize the benefits of contrast image enhancement according to new approaches described in this patent specification.

A breast imaging system according to examples described in this patent specification combines the capabilities of combined 2D and/or 3D breast x-ray imaging with benefits from contrast image acquisition processes. Biopsy capability (stereotactic or tomosynthesis guided) may also be integrated into the system, with lesion localization software utilizing any images selected from a group including simple 2D images, 3D projection images, 3D reconstructed data, or any of the 2D, 3D projection and 3D reconstructed data obtained during a dual energy or background subtraction image acquisition process.

With such arrangements, the following image protocols are supported:
Contrast imaging (background subtraction) using a single high or low energy image acquisition technique, in 2D or 3D mode.

Dual-energy contrast imaging in 2D or 3D mode;

Dual-energy contrast imaging in 3D mode, wherein high and low energy exposures occur at different angles during a tomosynthesis scan; [high and low energies can be reconstructed separately and combined to form the dual energy volume];

Dual-energy imaging in a combo system that acquires dual-energy 2D and dual-energy 3D images;

In combo imaging mode, where the 2D image data set is acquired using a single energy, and the 3D image data set is acquired using dual-energy imaging;

In combo imaging mode, where the 2D image data set is acquired using dual-energy imaging, and the 3D image data set is acquired using a single energy image;

Tomosynthesis imaging mode, wherein among a total of N views in a contrast tomo scan wherein the breast remains in compression throughout the scan, different projection images are allotted different, dose, kVps, mAs and filters for greater flexibility of different applications;

Tomosynthesis mode wherein a low energy scans and high energy scans alternate in a series of acquired projection images;

Tomosynthesis mode wherein low energy and high energy scans are performed for the projection images, in unequal ratios in user selectable patterns;

Stereotactic biopsy using contrast agent, and either dual energy or background subtraction imaging;

Upright biopsy using tomosynthesis scan images obtained using a contrast agent and either dual-energy or background subtraction imaging;

Other variations of combinations of contrast imaging and image acquisition modes are within the scope of this patent specification.

Image Acquisition Parameter Selection

Once an image acquisition mode and an acquisition process are identified, acquisition parameters and image processing techniques can be varied at a projection image granularity by varying at least one of kV, mA and/or filter for each 2D image capture.

Several modifications to existing mammography and/or tomosynthesis breast imaging systems may be made to support contrast imaging. For example, within the x-ray source, mechanisms that allow fast switching between kV, mA and x-ray beam filters may be provided to support dual-energy imaging between and within image capture modes. For example, an x-ray filter wheel may be provided to switch filters between low and high energy pulses. A variety of different filters, such as rhodium, silver, aluminum, copper and cesium iodide may be provided to provide the desired energy for different contrast agents.

Figure 3A:
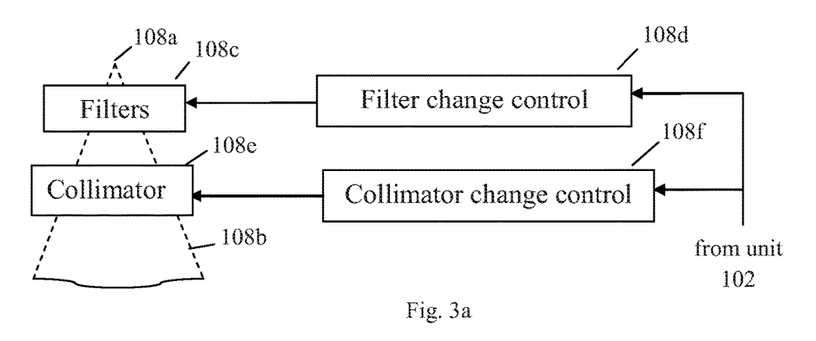
FIG. 3a illustrates an example of a variable filter/collimator mechanism.

FIG. 3a schematically illustrates an example where a focal spot 108a inside x-ray source 108 emits an imaging x-ray beam 108b toward an imaging x-ray receptor. The beam passes through a variable filter assembly 108c that contains a mechanism for interposing a selected filter in the beam path to thereby control the energy range of the x-rays that continue toward the imaging receptor. A filter change control 108d determines which filter will intercept the x-ray beam, and in turn is controlled by system settings or by a user through unit 102. Variable filter arrangement are known in the field, as they are used in a variety of systems, including dual energy bone densitometry systems of the type offered by the common assignee. A variable collimator 108e controls the area of the x-ray imaging beam at the imaging plane of the receptor, and is in turn controlled by a collimator controller 108f that can also receive commands from unit 102.

Figure 4:
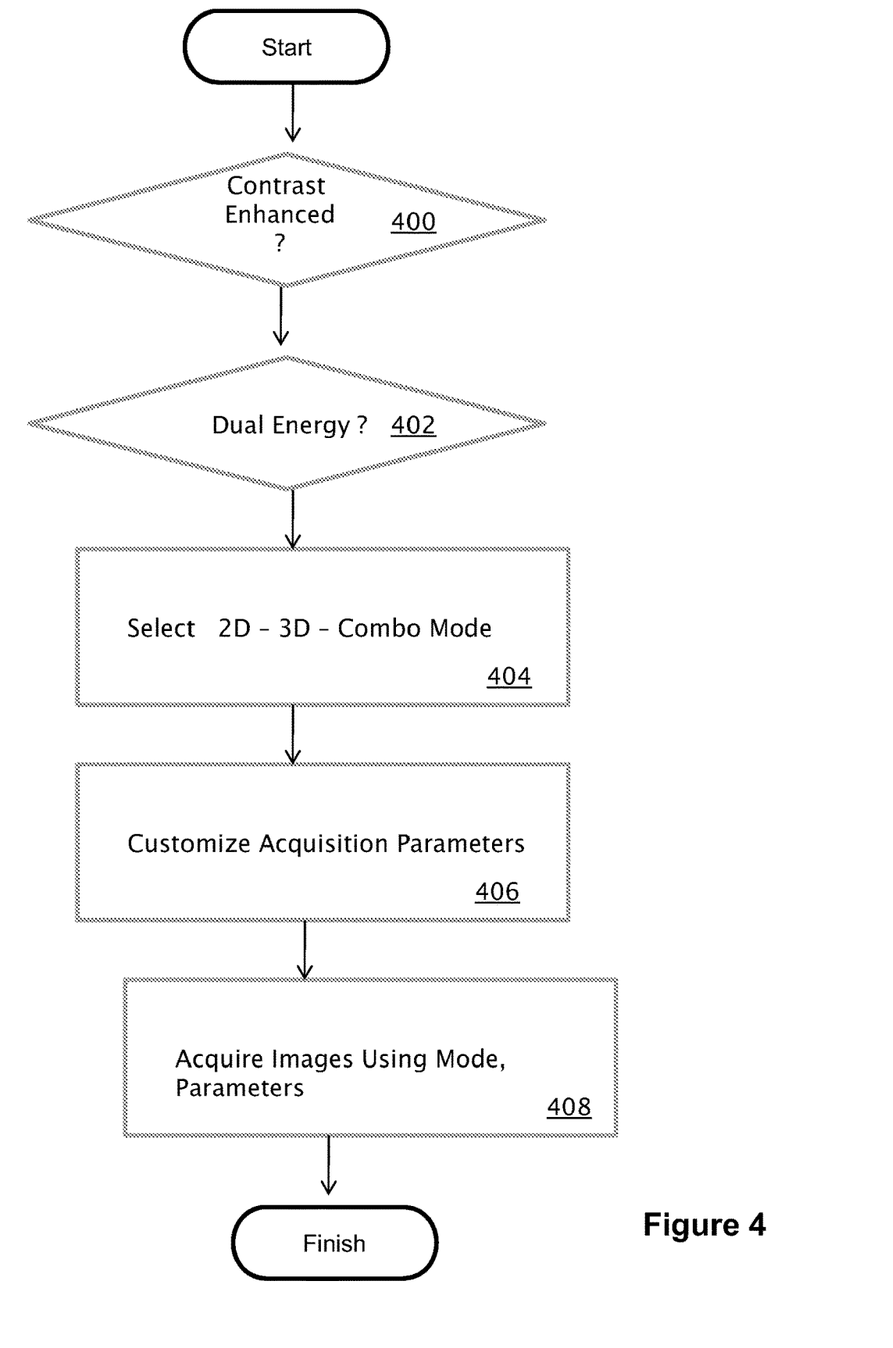
FIG. 4 illustrates steps in an example of operation of a breast imaging system.

The new systems described in this patent specification allow users to select physical acquisition parameters at a projection image granularity. For example, FIG. 4 illustrates an example of process steps that can be followed. In step 400 a decision is made whether to set the system to operate in a contrast-enhanced mode and in step 402 a decision is made whether to operate the system in a dual-energy mode. These decisions can be made by a user, or can be made automatically by the system depending on some information that a user enters. In step 404 the user or the system selects whether to operate in 2D mode only, in 3D mode only, or in a combination of 2D and 3D modes. In step 406, the system or the user may customize acquisition parameters such as kV, mAs, etc., and in step 408 the system operates with the settings selected in steps 400-406 to acquire images Tp and/or Mp.

Figure 5:
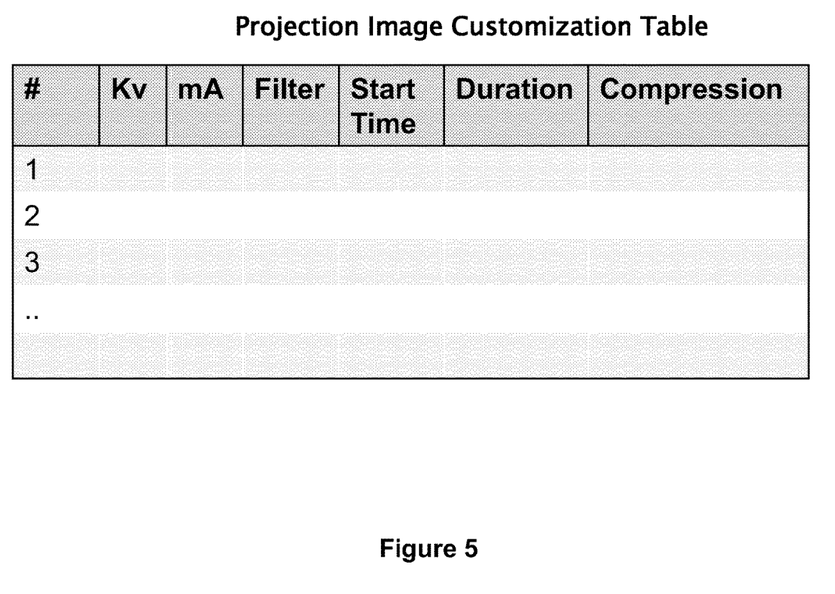
FIG. 5 illustrates a customization table for parameters used in carrying out breast imaging.

FIG. 5 illustrates an example of a tomosynthesis projection image customization table that may be presented to the user for manual customization of images of a tomosynthesis scan. Although certain fields are shown in the table, this patent specification anticipates that any acquisition variable may be made available to a user for customization of the image in this manner. Such a table may initially be populated with default values, which may be system defaults or default values populated following analysis of image data received in response to AEC, or may be filled in by a user and entered into the system.

Image Processing Selection

The new system also allows different image processing to be performed on received images, where the image processing techniques may be determined in response to a type of acquisition (i.e., a tomosynthesis acquisition, a 2D acquisition, a dual-energy acquisition, a contrast acquisition). Thus, for example, images acquired using high energy may be processed using different algorithms than images acquired using low energy. The image processing technique may be preprogrammed based on the selected acquisition mode or alternatively may be selected in response to user input. For the purposes of this patent specification, image processing refers to any manipulation and combination of the images, including noise filtering and in reconstruction. Some of the processing may be a function of the acquisition mode. For example, when performing background subtraction contrast imaging using tomosynthesis images, pre and post injection projection images may be subtracted, and the resulting signal shifted to register the images to compensate for patient motion.

In one embodiment, the new system enables the utilization of either gain controlled images or air-map corrected images as a basis for the contrast image processes (i.e., the images may be processed prior to the subtraction or addition processes). Gain controlled images are images that have been processed to compensate for system gain to increase SNR, for example using techniques described in said commonly assigned U.S. Pat. No. 7,991,106.

Display

A display of the new system may be used to display images captured using any of the modalities (2D, 3D, combo), using any image acquisition process. The display includes the ability to display the images in a variety of configurations, including singularly, side by side, toggled, or in cine-mode. With such an arrangement, a health professional may simultaneously view (or toggle between, or view in cine), the 2D image, 3D projection image or 3D slice image of a breast, at either the low energy acquisition, high energy acquisition, or following subtraction of the two, with or without the use of contrast agents, thereby enhancing the ability to visualize and characterize lesions.

Figure 6A:
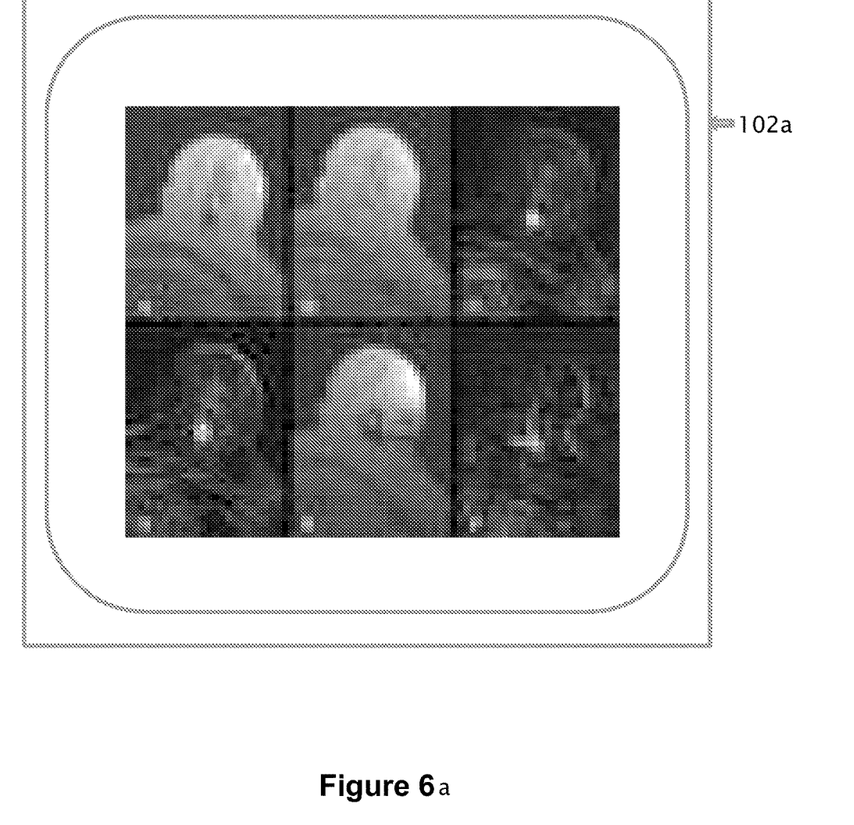
FIG. 6a illustrated a display of images taken in different aging modes of a system such as that illustrated in FIG. 2.
Figure 6B:
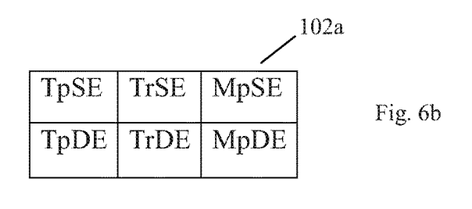
FIG. 6b schematically illustrates a display of ages taken in six different imaging modes of a system such as that of FIG. 1.

FIG. 6a illustrates an example in which different types of images are presented side-by-side, in respective windows of a computer display 102a. FIG. 6b schematically illustrates an example of computer display 102a that concurrently shows six different images of a patient's breast: a single-energy tomosynthesis projection image TpSE, a single-energy reconstructed tomosynthesis slice image TrSE, a single-energy mammogram MpSE, a dual-energy tomosynthesis projection image TpDE, a dual-energy reconstructed tomosynthesis slice image TrDE, and a dual-energy mammogram MpDE, It should be understood that in this context the term single-energy refers to the range of energies that an x-ray tube emits at a particular parameter setting of parameters that determine x-ray the energies that the tube emits, and the term dual energy refers to two such energy ranges that may partly overlap. It should also be understood that FIG. 6b illustrates one of the many examples of arranging images according to this patent specification, and that the image display may show only a subset of the illustrated images, may show images in a different relative arrangement, may show multiple images of the same kind (e.g., multiple images Tp, etc.), may show superimposed images, and/or may show images in cine mode, and may show a single image over the entire screen or may divide the screen into a different number of windows.

Figure 7:
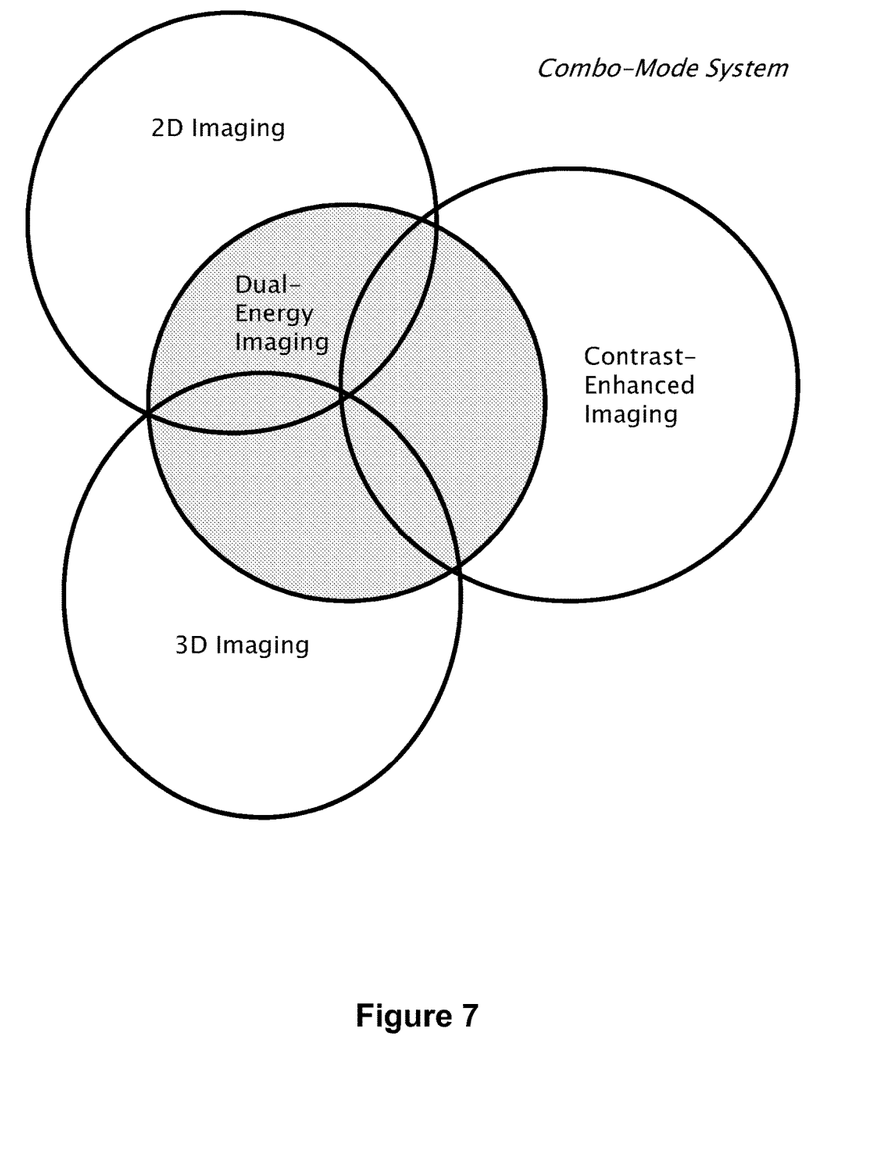
FIG. 7 illustrates possible combinations of imaging modes of a system such as illustrated in FIG. 1.
Figure 8:
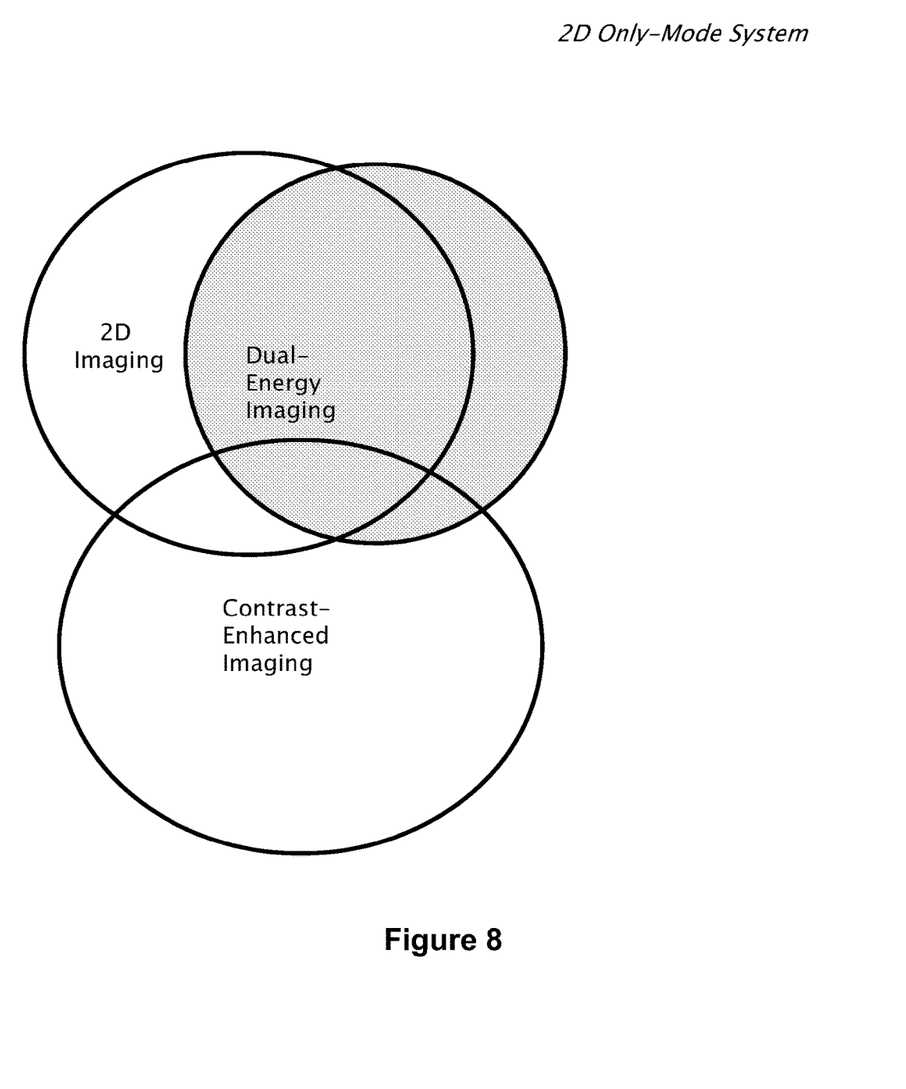
FIG. 8 is a similar illustration of possible combinations of imaging modes in a system that takes only 2D images.
Figure 9:
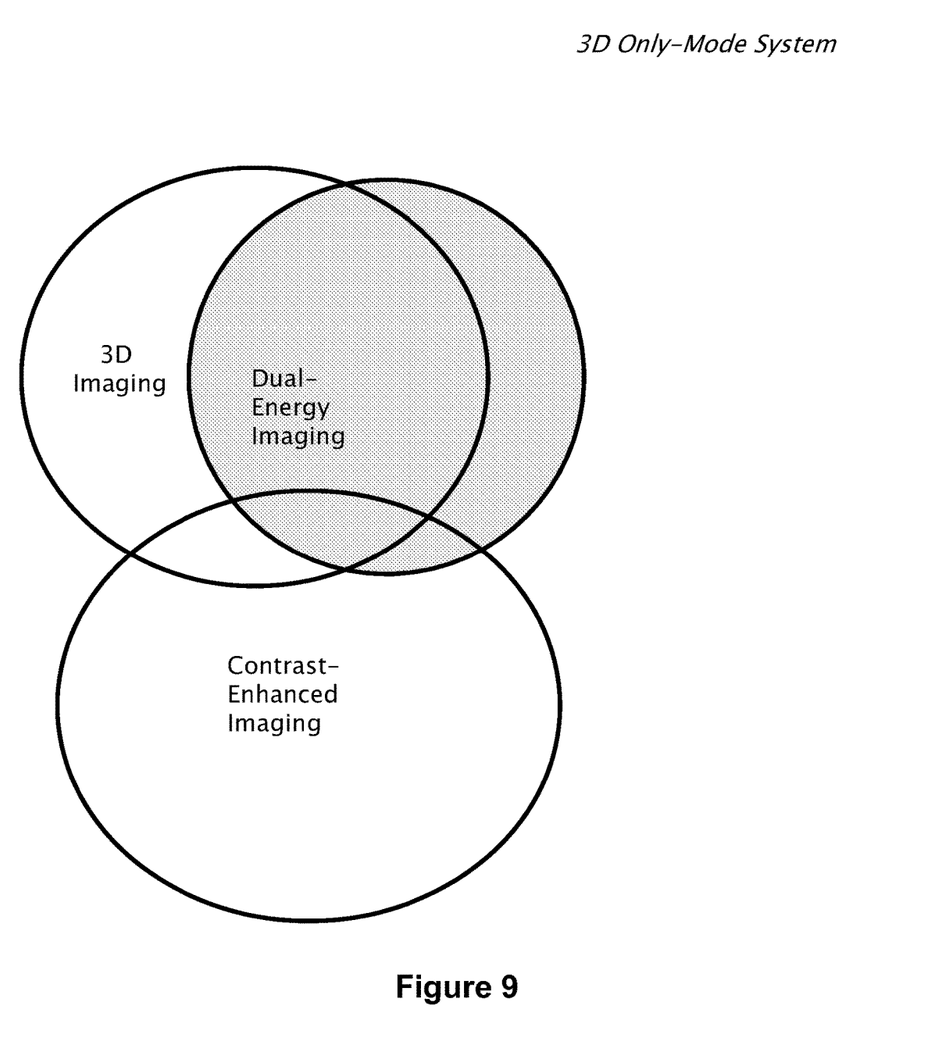
FIG. 9 is a similar illustration of possible combinations of imaging modes in a system that takes only 3D images.

FIG. 7 illustrates a scope of imaging in different modes of operation, of a combo system that operates in either or both of a 2D imaging mammography mode and a 3D imaging tomosynthesis mode. In each of these 2D and 3D modes, the system can operate image the breast with or without contrast agent in the breast. In either or both of the 2D and 3D modes, and with or without contrast agent in the breast, the system can carry out dual-energy imaging or background subtraction imaging. As seen in FIG. 7, these capabilities allow for many different combinations of modes such as 2D using single-energy (SE) and contrast enhancement (CE), 2D using SE, 3D using CE, 3D using DE, etc. FIG. 8 illustrates a scope of imaging when using a 2D only system, i.e., a system that does not include 3D tomosynthesis capabilities. In the FIG. 8 example, the system can be used in single-energy or dual-energy modes, in each case with or without contrast agent in the breast. FIG. 9 illustrates the operation of a 3D only system that can operate in 3D imaging mode using single-energy or dual-energy imaging, in either case with or without contrast agent in the breast.

Although the above has described the use of the new system with regard to acquisition of both tomosynthesis and mammogram images, this patent specification is not limited to an integrated multi-mode system but applies to any system that is capable of performing tomosynthesis. For example the new system may include only tomosynthesis imaging capability. Such systems may use a legacy mammogram for example for calcification detection, or may obtain a single tomosynthesis image at higher dosage to use as their 2D image, or may synthesize a mammogram image from tomosynthesis projection images. In addition, the new system may incorporate tomosynthesis imaging capability with a different modality, such as molecular breast imaging or ultrasound imaging. In short any breast imaging systems which includes tomosynthesis imaging capabilities falls within the scope of this patent specification. Still in addition, some of the improvements described in this patent specification also apply to systems that take only 2D images.

The above specific examples and embodiments are illustrative, and many variations can be introduced on these examples and embodiments without departing from the spirit of the disclosure or from the scope of the appended claims. For example, elements and/or features of different illustrative embodiments may be combined with each other and/or substituted for each other within the scope of this disclosure and appended claims.

Preferred Examples

In a preferred example, the system described in this patent specification obtains (i) 3D tomosynthesis slice images TrSE of a patient's breast that represent respective slices of the breast and are reconstructed through computer-processing of a multiplicity of single-energy x-ray 2D tomosynthesis projection images TpSE of the patient's breast, (ii) a low-energy x-ray 2D mammogram MpL, and (ii) a high-energy x-ray 2D mammogram MpH of the breast. The Tp, MpL and MpH images preferably are taken in a single breast compression, while the breast remains immobilized. The system computer-processes the 2D low-energy mammogram MpL and the 2D high-energy mammogram MpH to form a weighted combination dual-energy 2D mammogram image MpCDE that tends to highlight vascularity in the breast. The system displays, preferably concurrently, (i) the combination 2D image MpCDE, which can help reveals positions of possible vascular abnormalities in two dimensions, and (ii) 3D slice images TrSE in which the abnormalities appear and which can help reveal 3D positions of the abnormalities and the appearance of the abnormalities in the slice images.

Preferably, the system is configured to respond to an identification of an abnormality in the MpCDE image to automatically identify the subset of TrSE images in which the abnormality appears. Also preferably, the system is configured to concurrently display the MpCDE image and either one or more but not all of the images of said subset of TrSE images, or the entire subset.

Figure 10:
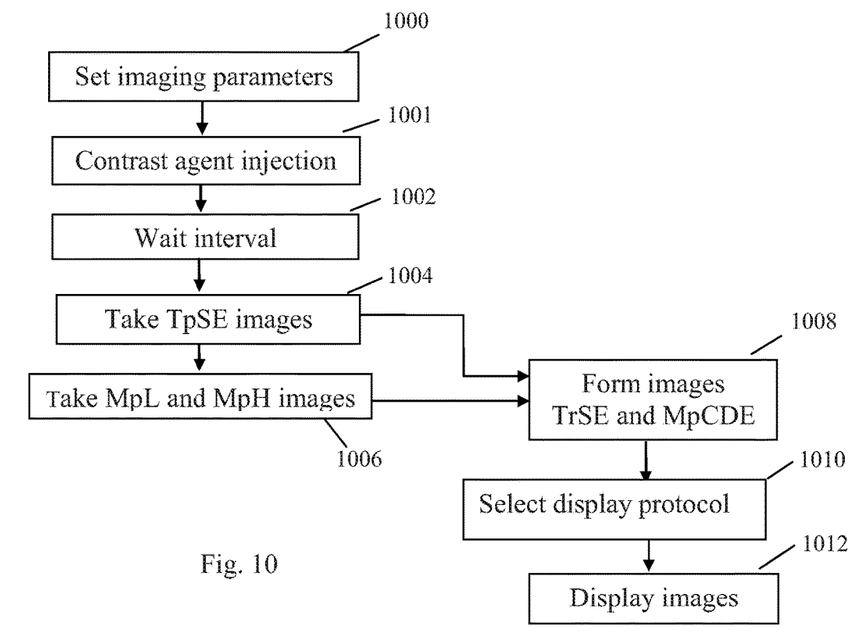
FIG. 10 illustrates steps in a preferred example of operation of a system such as illustrated in FIG. 1.

FIG. 10 illustrates steps of a method for carrying out imaging according to the preferred example. In step 1000, imaging parameters such as those illustrated in FIG. 4 are set for an imaging sequence. This can be done either by storing a default in the system, e.g., in acquisition workstation 102 shown in FIG. 1, or more typically by selecting parameters adapted to a particular patient and/or a particular study, using for example a table such as illustrated in FIG. 5. In step 1001, a contrast agent is injected, such as a standard FDA-approved low osmolarity Iodine contrast agent. In one example, 350-370 mg/ml of the contrast agent are injected at a rate of 3 to 3.5 ml/sec, or within safety parameters of the IV gauge in place, with a total volume of 1.5 ml/kg patient weight up to a maximum of 150 ml. In general, the agent can be the same as commonly used clinically for contrast-enhanced CT scanning of the chest and abdomen. The injection can be be in the antecubital or forearm vein. Step 1002 is waiting time, typically of the order of a minute or two after the start of the injection. The duration of step 1002 is set based on health professionals' assessment of the time needed for the contrast agent to reach a desirable concentration in the breast. In step 1004, the patient's breast is compressed in the manner known for tomosynthesis images and a system such as that illustrated in FIG. 1, or such as the Selenia® Dimensions® available from the assignee, operates in a single-energy tomosynthesis mode to take plural single-energy projection images TpSE of the breast, for example 22 images TpSE, each from a respective different angle of the imaging x-ray beam relative to the breast, over an angular range such as ±15°. In step 1006 and while the patient's breast remains compressed and immobilized, the system takes a low-energy mammogram MpL and a high-energy mammogram MpH, for example by returning the x-ray source to a 0° position and taking the image MpL with one x-ray filter in the imaging x-ray beam, then changing to a different x-ray filter and taking the image MpH. Preferably, x-ray energies in the 30-40 kVp range are used for the TrSE images, less than 35 kVp (e.g., in the 28-30 kVp range) for the MpL image, and more than 45 kVp (e.g., in the 45-49 kVp range) for the MpH image. However, different energies can be used in a manner consistent with clinical practice. As one example, a Rhodium or Silver x-ray filter can be used for the MpL image but a Copper filter for the MpH image. The other imaging parameters follow typical clinical practice and may depend on factors such as the thickness and x-ray density of the compressed breast.

In step 1008, the TpSE images are computer-processed to form TrSE images, using reconstruction algorithms of the type described in the material incorporated by reference, and the MpL and MpH images are computer-processed to form a combined image MpCDE. For example, the combined image is obtained according to the relationship MpCDE=MpH−kMpL, where k is a weighting factor and typically k>1, as is known in the dual-energy x-ray imaging technology. In step 1010, a display protocol is selected, either automatically according to a preset default protocol or as selected by a user for a particular patient study or a particular display, and can be set into a workstation such as unit 102 of FIG. 1 or into a separate imaging workstation. In step 1012 one or more of the images TrSE and MpCDE are displayed on a screen such as screen 102a shown in FIG. 6b. In addition, other images can be displayed on the same screen or other screens, such as any of the images TpSE and other images such as images of the breast obtained at other times with the same or different modalities such as, without limitation, MRI, CT, nuclear medicine imaging devices, and ultrasound Numerous variations are possible in the order of steps illustrated in FIG. 10. For example, the order of steps 1004 and 1006 can be reversed. Step 108 can start before step 1006, or well after step 1006. Steps 1008, 1010 and 1012 can be carried out in devices remote from unit 100 illustrated in FIG. 1.

It should be appreciated that the preferred example illustrated above is only one of many examples consistent with this patent specification, and that other combination of modes and steps also are within the scope of the specification.

The invention claimed is:

1. A method of multi-mode x-ray examination of a patient's breast comprising:
    compressing the patient's breast, using a single compression, substantially between an x-ray source and an imaging x-ray detector;
    acquiring, during the single compression of the patient's breast, a plurality of tomosynthesis projection images and a plurality of 2D x-ray mammogram projection images, wherein:
        a first subset of the plurality of tomosynthesis projection images is acquired using a different x-ray energy than a second subset of the plurality of tomosynthesis projection images and the plurality of 2D x-ray mammogram projection images; and
        a first subset of the plurality of 2D x-ray mammogram projection images is acquired using a different x-ray energy than a second subset of the plurality of 2D x-ray mammogram projection images;
    computer-processing the plurality of tomosynthesis projection images to obtain a plurality of dual-energy reconstructed tomosynthesis slice images;
    computer-processing the plurality of 2D x-ray mammogram projection images to obtain a combined dual-energy 2D mammogram image; and
    displaying at least one of: one or more of the plurality of dual-energy reconstructed tomosynthesis slice images or the combined dual-energy 2D mammogram image.

2. The method of claim 1, wherein the displaying comprises concurrently displaying the one or more of the plurality of dual-energy reconstructed tomosynthesis slice images and the combined dual-energy 2D mammogram image.

3. The method of claim 2, wherein the concurrently displaying the one or more of the plurality of dual-energy reconstructed tomosynthesis slice images and the combined dual-energy 2D mammogram image comprises concurrently displaying the one or more of the plurality of dual-energy reconstructed tomosynthesis slice images and the combined dual-energy 2D mammogram image side by side.

4. The method of claim 2, wherein the concurrently displaying the one or more of the plurality of dual-energy reconstructed tomosynthesis slice images and the combined dual-energy 2D mammogram image comprises concurrently displaying more than one of the plurality of the dual-energy reconstructed tomosynthesis slice images and the combined dual-energy 2D mammogram image.

5. The method of claim 1, wherein the displaying comprises concurrently displaying the combined dual-energy 2D mammogram image and a subset of the plurality of the dual-energy reconstructed tomosynthesis slice images, wherein the subset of the plurality of dual-energy reconstructed tomosynthesis slice images comprises slice images in which abnormalities appear and the subset of the plurality of dual-energy reconstructed tomosynthesis slice images is automatically selected in response to an identification of the abnormality in the combined dual-energy 2D mammogram image.

6. The method of claim 1 wherein the acquiring step comprises acquiring, first, the plurality of tomosynthesis projection images, and then acquiring, second, the plurality of 2D x-ray mammogram projection images.

7. The method of claim 1 wherein the acquiring step comprises acquiring one half of the plurality of tomosynthesis projection images in the first subset of the plurality of tomosynthesis projection images and acquiring the other half of the plurality of tomosynthesis projection images in the second subset of the plurality of tomosynthesis projection images.

8. The method of claim 1, wherein the x-ray source, and the imaging x-ray detector are in an upright system.

9. The method of claim 1 further comprising acquiring one of the subsets of the plurality of tomosynthesis projection images at an x-ray energy level between 30-40 kVp.

10. A system multi-mode x-ray examination of a patient's breast, the system comprising:
    an x-ray source capable of selectively moving relative to a patient's breast;
    an imaging x-ray detector;
    a compression mechanism disposed between the x-ray source and the imaging x-ray detector;
    a control module programmed with a set of instructions that when executed cause the system to perform a set of operations, comprising:

compressing the patient's breast, using a single compression, substantially between an x-ray source and an imaging x-ray detector;

acquiring, during the single compression of the patient's breast, a plurality of tomosynthesis projection images and a plurality of 2D x-ray mammogram projection images wherein:

a first subset of the plurality of tomosynthesis projection images is acquired using a different x-ray energy than a second subset of the plurality of tomosynthesis projection images and the plurality of 2D x-ray mammogram projection images; and a first subset of the plurality of 2D x-ray mammogram projection images is acquired using a different x-ray energy than a second subset of the plurality of 2D x-ray mammogram projection images;

computer-processing the plurality of tomosynthesis projection images to obtain a plurality of dual-energy reconstructed tomosynthesis slice images;

computer-processing the plurality of 2D x-ray mammogram projection images to obtain a combined dual-energy 2D mammogram image; and displaying at least one of: one or more of the plurality of dual-energy reconstructed tomosynthesis slice images or the combined dual-energy 2D mammogram image.

11. The system of claim 10, wherein the displaying further comprises concurrently displaying the one or more of the plurality of dual-energy reconstructed tomosynthesis slice images and the combined dual-energy 2D mammogram image.

12. The system of claim 11, wherein the concurrently displaying the one or more of the plurality of dual-energy reconstructed tomosynthesis slice images and the combined dual-energy 2D mammogram image further comprises concurrently displaying the one or more of the plurality of dual-energy reconstructed tomosynthesis slice images and the combined dual-energy 2D mammogram image side by side.

13. The system of claim 11, wherein the concurrently displaying the one or more of the plurality of dual-energy reconstructed tomosynthesis slice images and the combined dual-energy 2D mammogram image further comprises concurrently displaying more than one of the plurality of the dual-energy reconstructed tomosynthesis slice images and the combined dual-energy 2D mammogram image.

14. The system of claim 10, wherein the displaying comprises concurrently displaying the combined dual-energy 2D mammogram image and a subset of the plurality of the dual-energy reconstructed tomosynthesis slice images, wherein the subset of the plurality of dual-energy reconstructed tomosynthesis slice images comprises slice images in which abnormalities appear and the subset of the plurality of dual-energy reconstructed tomosynthesis slice images is automatically selected in response to an identification of the abnormality in the combined dual-energy 2D mammogram image.

15. The system of claim 10, wherein the acquiring operation comprises acquiring, first, the plurality of tomosynthesis projection images, and then acquiring, second, the plurality of 2D x-ray mammogram projection images.

16. The system of claim 10, wherein the acquiring operation comprises acquiring one half of the plurality of tomosynthesis projection images in the first subset of the plurality of dual-energy reconstructed tomosynthesis and acquiring the other half of the plurality of tomosynthesis projection images in the second subset of the plurality of dual-energy reconstructed tomosynthesis.

17. The system of claim 10, wherein the system is an upright system.

18. The system of claim 10, wherein the operations further comprise acquiring one of the subsets of the plurality of tomosynthesis projection images at an x-ray energy level between 30-40 kVp.

\* \* \* \* \*